United States Patent [19]
Silverman et al.

[11] Patent Number: 6,117,854
[45] Date of Patent: Sep. 12, 2000

[54] ENHANCED PERFORMANCE INSECTICIDE COMPOSITIONS CONTAINING PLANT DERIVED OIL CARRIERS AND METHODS OF USING THE SAME

[75] Inventors: Jules Silverman, Walnut Creek; Theodore J. Shapas, Danville, both of Calif.

[73] Assignee: The Clorox Company, Oakland, Calif.

[21] Appl. No.: 08/914,775

[22] Filed: Aug. 20, 1997

[51] Int. Cl.[7] .......................... A01N 57/00; A01N 43/56; A01N 43/02
[52] U.S. Cl. ..................... 514/89; 514/407; 514/450
[58] Field of Search ................. 514/340, 89, 407, 514/450

[56] References Cited

U.S. PATENT DOCUMENTS

| | | | |
|---|---|---|---|
| Re. 30,740 | 9/1981 | Frensch et al. | 424/276 |
| 3,630,446 | 12/1971 | Roth et al. | 239/60 |
| 3,636,207 | 1/1972 | Bouvet et al. | 429/219 |
| 3,937,826 | 2/1976 | Harris | 424/219 |
| 3,952,102 | 4/1976 | Albrecht et al. | 424/276 |
| 3,961,040 | 6/1976 | Rabussier et al. | 424/78 |
| 3,996,375 | 12/1976 | Frensch et al. | 424/276 |
| 4,278,014 | 7/1981 | Knieps | 100/261 |
| 4,320,130 | 3/1982 | Balsley et al. | 424/251 |
| 4,349,981 | 9/1982 | Sherman | 43/131 |
| 4,353,907 | 10/1982 | Lovell | 424/251 |
| 4,368,591 | 1/1983 | Barke et al. | 47/57 |
| 4,510,133 | 4/1985 | Evans | 514/30 |
| 4,560,677 | 12/1985 | Dybas | 514/30 |
| 4,626,528 | 12/1986 | McHenry | 514/119 |
| 4,657,912 | 4/1987 | Suzuki et al. | 514/275 |
| 4,681,900 | 7/1987 | Iwasaki | 514/706 |
| 4,696,822 | 9/1987 | Matsumura et al. | 424/490 |
| 4,721,706 | 1/1988 | Bessler et al. | 514/78 |
| 4,750,934 | 6/1988 | Metzner et al. | 106/18 |
| 4,796,381 | 1/1989 | Kauth et al. | 43/124 |
| 4,874,611 | 10/1989 | Wilson et al. | 424/410 |
| 4,902,510 | 2/1990 | Garden | 424/405 |
| 4,929,608 | 5/1990 | Mahmood | 514/122 |
| 4,950,682 | 8/1990 | Pap et al. | 514/417 |
| 4,985,413 | 1/1991 | Kohama et al. | 514/79 |
| 4,996,053 | 2/1991 | Hatcher | 424/410 |
| 5,023,183 | 6/1991 | Friedman et al. | 435/240.3 |
| 5,026,734 | 6/1991 | Browning | 514/723 |
| 5,063,084 | 11/1991 | Nelson | 427/154 |
| 5,120,540 | 6/1992 | Doane et al. | 424/195.1 |
| 5,130,135 | 7/1992 | Van Tonder | 424/405 |
| 5,196,407 | 3/1993 | Goletz et al. | 514/63 |
| 5,198,467 | 3/1993 | Milks | 514/553 |
| 5,221,535 | 6/1993 | Domb | 424/450 |
| 5,248,086 | 9/1993 | Waldrum et al. | 239/10 |
| 5,248,450 | 9/1993 | Metzner et al. | 252/380 |
| 5,271,179 | 12/1993 | Cohen | 43/131 |
| 5,401,506 | 3/1995 | Chang et al. | 424/408 |
| 5,417,973 | 5/1995 | King | 424/195.1 |
| 5,434,181 | 7/1995 | Kodaka et al. | 514/471 |
| 5,435,992 | 7/1995 | Audegond et al. | 424/195.1 |
| 5,439,683 | 8/1995 | Hodakowski | 424/408 |
| 5,464,613 | 11/1995 | Barcay et al. | 424/84 |
| 5,464,618 | 11/1995 | Doane et al. | 424/195.1 |
| 5,498,624 | 3/1996 | McLoughlin et al. | 514/406 |
| 5,554,576 | 9/1996 | Mookerjee et al. | 514/125 |
| 5,580,567 | 12/1996 | Roberts | 424/84 |
| 5,756,474 | 5/1998 | Furstenau | 514/30 |
| 5,849,320 | 12/1998 | Turnblad et al. | 424/410 |

FOREIGN PATENT DOCUMENTS 2070799  12/1996  Russian Federation.

OTHER PUBLICATIONS

Abstract of EP 311 180 (Apr. 12, 1989).
Abstract of GB 2113092 (Aug. 3, 1983).
Abstract of GB 2058569 (Apr. 15, 1981).
Abstract of JP 61–254507 (Nov. 12, 1986).
Abstract of JP 61–22003 (Jan. 30, 1986).
Abstract of JP 60–255701 (Dec. 17, 1985).
Abstract of JP 57–171906 (Oct. 22, 1982).
Abstract of JP 57–154113 (Sep. 22, 1982).
Abstract of JP 56–169601 (Dec. 26, 1981).
Abstract of JP 56–138105 (Oct. 28, 1981).
Abstract of JP 56–65808 (Jun. 3, 1981).
Abstract of JP 56–8308 (Jan. 28, 1981).
Abstract of JP 55–31053 (Mar. 5, 1980).
Abstract of JP 07–304603 (Nov. 21, 1995).
Abstract of JP 02–307912 (Dec. 21, 1990).
Abstract of JP 02–207009 (Aug. 16, 1990).
Abstract of JP 02–67204 (Mar. 7, 1990).
Abstract of JP 02–67203 (Mar. 7, 1990).
Abstract of JP 01–301605 (Dec. 5, 1989).
Abstract of JP 01–151501 (Jun. 14, 1989).
Abstract of JP 01–38004 (Feb. 8, 1989).
Abstract of JP 63–218604 (Sep. 12, 1988).
Abstract of JP 62–198602 (Sep. 2, 1987).
Abstract of JP 62–195301 (Aug. 28, 1987).
Abstract of WO 92/19429 (Nov. 12, 1992).
Abstract of WO 92/10170 (Jun. 25, 1992).
Abstract of WO 96/31123 (Oct. 10, 1996).
Philip G. Koehler et al., "Control of German Cockroach (Dictyoptera: Blattellidae) with Residual Toxicants in Bait Trays", *Journal of Economic Entomology*, vol. 89, No. 6, pp. 1491–1496 (1996).

*Primary Examiner*—Jose' G. Dees
*Assistant Examiner*—Alton Pryor
*Attorney, Agent, or Firm*—Harry A. Pacini; Mark D. Sweet

[57] ABSTRACT

A composition effective for the control of insects is disclosed, wherein the composition contains a phenyl pyrazole compound, a halopyridyl compound, or an avermectin compound, or combinations thereof, and a plant-derived oil carrier. Also disclosed is a method of applying the composition to an area where the insects are to be controlled. The composition may be applied to discrete locations within the area, or applied to a substrate with the substrate then being placed within the area.

32 Claims, 8 Drawing Sheets

ENHANCED PERFORMANCE INSECTICIDE COMPOSITIONS CONTAINING PLANT DERIVED OIL CARRIERS AND METHODS OF USING THE SAME

FIELD OF INVENTION

Our discovery relates to compositions effective for controlling insects, and more particularly, compositions containing phenyl pyrazole compounds and plant-derived oil carriers.

BACKGROUND OF INVENTION

Compositions for controlling insects such as cockroaches are known in the art. Generally, the compositions contain at least one substance toxic to the insects, and may be applied by spraying an area where the insects are to be controlled, or applying the composition over a random and/or substantially continuous region within the area by some other technique.

U.S. Pat. No. 5,580,567 represents an example of such a spraying technique, where the composition may contain, among other things, a vegetable oil as a "spray oil." The "spray oil" is used to provide a one-step addition of adjuvants to obtain a more uniform spread of the spray solution over the treated area, improved penetration, and slower evaporation.

U.S. Pat. No. 4,985,413 discloses the use of compositions containing vegetable oils and insecticides for the control of cockroaches, where the compositions may be pressed into a tablet form.

U.S. Pat. No. 5,232,940 describes generally N-phenyl pyrazole derivatives and their use in compositions against arthropod, plant nematode, helminth, and protozoan pests.

Compositions for controlling insects may have undesirable effects on humans and domesticated animals. These compositions may also carry unpleasant odors, or have a stickiness rendering them less desirable for many uses. Accordingly, a need exists for compositions and methods that effectively control insects while minimizing these undesirable aspects.

OBJECTS OF THE INVENTION

An object of the invention is to provide a composition suitable for use in controlling insects.

Another object of the invention is to provide a composition having superior efficacy for controlling insects.

Another object of the invention is to provide a method of controlling insects that reduces the total area to which the composition needs to be applied.

SUMMARY OF THE INVENTION

To achieve these and other objectives, and in accordance with the purpose of our invention as embodied and broadly described herein, in one aspect we describe a composition having an active ingredient in an amount toxic to insects wherein the active ingredient is a phenyl pyrazole compound, a halopyridyl compound, an avermectin compound or combinations thereof; and a plant-derived oil carrier.

In another aspect we describe a method of controlling insects, where the method includes application of a composition containing (a) an active ingredient selected from the group consisting of a phenyl pyrazole compound, a halopyridyl compound, and an avermectin, and (b) a plant-derived oil carrier; to an area where the insects are to be controlled.

DETAILED DESCRIPTION OF THE INVENTION

Figure 1:
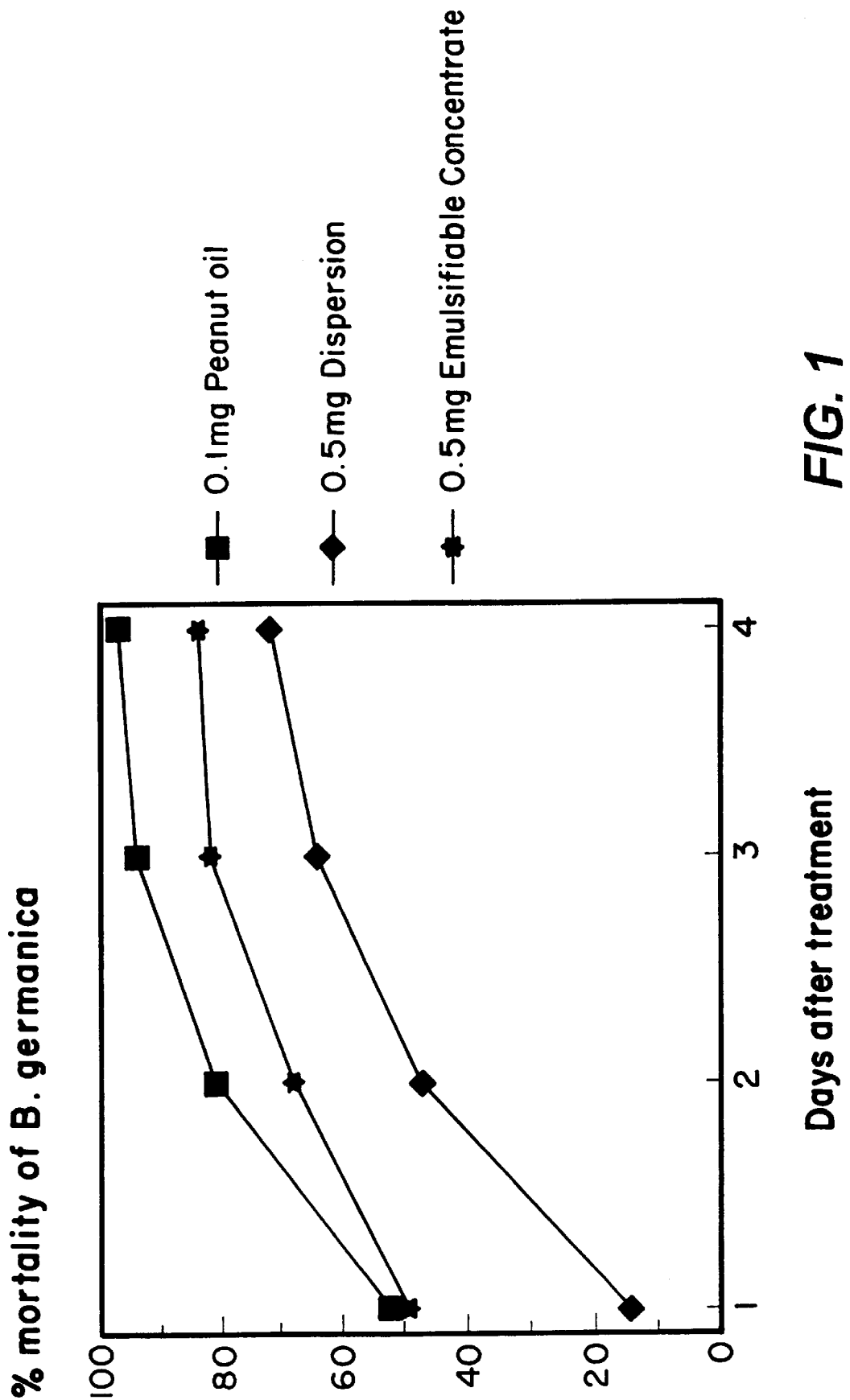
FIG. 1 is a graph comparing the mortality rates of various compositions containing fipronil.
Figure 2:
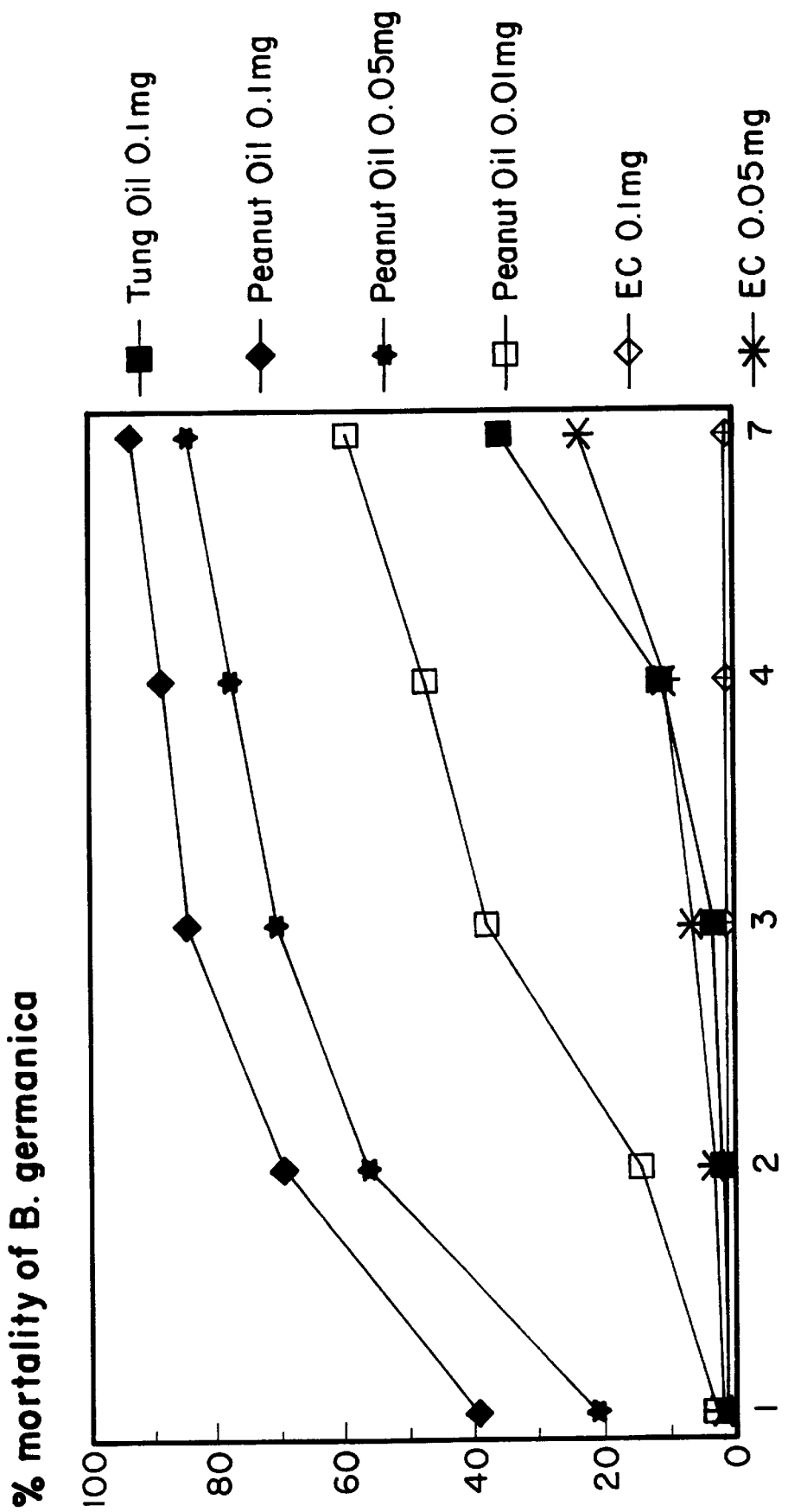
FIG. 2 is a graph comparing the mortality rates of various compositions containing fipronil.

As mentioned, conventional compositions for controlling insects, such as cockroaches, are typically applied by the random and/or substantially continuous application of the compositions to be treated in order to maximize the composition's efficacy. Such an application adds to the expense and waste of the product, may have undesirable environmental and safety consequences, and reduces the desirability of using such compositions in the home or workplace.

In accordance with the invention, however, our composition comprises a phenyl pyrazole compound, a halopyridyl compound, or an avermectin compound, and a plant-derived oil carrier where the composition does not need to be applied in such a random and/or substantially continuous manner. These components, particularly the phenyl pyrazole compounds compounds, have substantially no repellant properties with respect to insects such as cockroaches and ants. As a result, a discrete application of our composition has substantial effect in controlling the insects.

As used herein, "a phenyl pyrazole compound" refers to the compounds referred to as N-phenylpyrazole derivatives in U.S. Pat. No. 5,232,940. The entire contents of the '940 patent are incorporated herein by reference.

More specifically, the phenyl pyrazole compound used in our composition will have the following chemical structure,

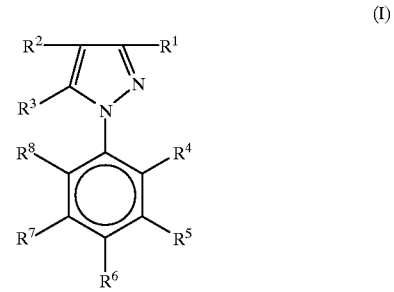

(I)

wherein $R^1$ represents a cyano or nitro group, a halogen, i.e. fluorine, chlorine, bromine or iodine atom, an acetyl or formyl group, a straight- or branched-chain alkyl group containing from 1 to 4 carbon atoms which may be unsubstituted or substituted by one or more halogen atoms or a cycloalkyl group containing from 3 to 6 carbon atoms; $R^2$ represents a group R'SO$_2$, R'SO, or R'S in which R' represents a straight- or branched-chain alkyl, alkenyl or alkynyl (preferably 1-(alkynyl)alkyl and more preferably alk-2-ynyl) group containing up to 6 carbon atoms which may be unsubstituted or substituted by one or more halogen atoms which may be the same or different; or R$^2$ is a halogen, i.e., fluorine, chlorine, bromine or iodine atom, a cyano or nitro group, a cycloalkyl group containing from 3 to 5 carbon atoms, a straight- or branched-chain alkenyl group containing from 2 to 6 carbon atoms, a thiocyanato group, a sulphamoyl group which may be unsubstituted or substituted by one or two straight- or branched-chain alkyl groups which may be the same or different and contain from 1 to 6 carbon atoms, a carbamoyl group which may be unsubstituted or substituted by one or two straight- or branched-chain alkyl groups which may be the same or different and contain from 1 to 6 carbon atoms, a straight- or branched-chain alkoxycarbonyl containing from 2 to 7 carbon atoms, a straight- or branched-chain alkanoyl group containing from 2 to 7 carbon atoms, or a straight- or branched-chain alkyl group containing from 1 to 6 carbon atoms which may be unsubstituted or substituted by one or more halogen atoms; R$^3$ represents a hydrogen atom, or an amino group —NR"R'" wherein R" and R'", which may be the same or different, each represent a hydrogen atom or a straight- or branched-chain alkenylalkyl or alkynylalkyl group containing up to 5 carbon atoms, a straight- or branched-chain alkyl group (containing from 1 to 6 carbon atoms, and which may be unsubstituted or substituted by straight- or branched-chain alkoxycarbonyl of 2 to 5 carbon atoms), a formyl group, a straight- or branched-chain alkanoyl group (which contains from 2 to 7 carbon atoms and which may be optionally substituted with one or more halogen atoms) or R" and R'", together with the nitrogen atom to which they are attached, form a 5 to 6 membered cyclic imide and is unsubstituted or substituted with one or more halogen atoms, or R$^3$ represents a straight- or branched-chain alkoxycarbonyl group (which contains from 2 to 7 carbon atoms and is unsubstituted or substituted by one or more halogen atoms), or R$^3$ represents a straight- or branched-chain alkoxymethyleneamino group containing from 2 to 5 carbon atoms which may be unsubstituted or substituted on methylene by a straight- or branched-chain alkyl group containing from 1 to 4 carbon atoms, or R$^3$ represents a halogen, i.e., fluorine, chlorine, bromine or iodine, a cycloalkyl group containing from 3 to 6 carbon atoms, or cycloakylcarbonyl group (which contains from 4 to 7 carbon atoms) or straight- or branched-chain alkoxy carbonyl group (which contains from 2 to 7 carbon atoms which are unsubstituted or substituted by one or more halogen atoms), or R$^3$ represents a straight- or branched-chain alkylsulphenylamino group containing from 1 to 4 carbon atoms, or R$^3$ represents a straight- or branched-chain alkyl group containing from 1 to 4 carbon atoms, the carboxy group or a straight-branched chain alkylthio, alkylsulphinyl or alkysulphonyl group containing from 1 to 6 carbon atoms which may be unsubstituted or substituted by one or more halogen atoms, or R$^3$ represents a straight- or branched-chained trialkylsilylmethyl group containing from 1 to 6 carbon atoms in each alkyl group which may be the same or different, a trialkyl-silyl group containing from 1 to 6 carbon atoms in each alkyl group which may be the same or different, or the cyano or nitro group; R$^4$, R$^5$, R$^6$, R$^7$ and R$^8$ may be the same or different and represent a halogen, i.e., fluorine, chlorine, bromine or iodine, a straight- or branched-chain alkyl or alkoxy group containing from 1 to 4 carbon atoms which may be unsubstituted or substituted by one or more halogen atoms (e.g. a trifluoromethyl or trifluoromethoxy group), a straight- or branched-chain alkylthio or alkylsulphinyl group containing from 1 to 4 carbon atoms which is substituted by one or more halogen atoms (e.g. a trifluoromethylthio or trifluoromethylsulphinyl group), the nitro or cyano group or a straight- or branched-chain alkylsulphonyl group containing from 1 to 4 carbon atoms which may be unsubstituted or substituted by one or more halogen atoms (e.g. the trifluoromethylsulphonyl group).

Preferably, phenyl pyrazole compounds of the above formula are used wherein R$^1$ represents a cyano or nitro group, a halogen, i.e., fluorine, chlorine, bromine, or iodine, atom, or an acetyl or formyl group; R$^2$ represents group R'SO$_2$, R'SO, or R"S in which R' represents a straight or branched chain alkyl, alkenyl or alkynyl (preferably 1-(alkynyl) alkyl and more preferably alk-2-ynyl) group containing up to 4 carbon atoms which may be unsubstituted or substituted by one or more halogen atoms which may be the same of different; R$^3$ represents a hydrogen atom, or an amino group —NR'R'" wherein R" and R'", which may be the same or different, each represent a hydrogen atom or a straight or branched chain alkyl, alkenyl or alkynylalkyl group containing up to 5 carbon atoms, a formyl group, a straight or branched chain alkanoyl group (which contains from 2 to 5 carbon atoms and which may be optionally substituted by one or more halogens atoms) or R" and R'" together with the nitrogen atom to which they are attached form a 5 or 6 membered cyclic imide, or represents a straight or branched-chain alkoxycarbonyl group (which contains 2 to 5 carbon atoms and is unsubstituted or substituted by one or more halogen atoms), or R$^3$ represents a straight or branched-chain alkoxymethyleneamino group containing from 2 to 5 carbon atoms which may be unsubstituted or substituted on methylene by a straight or branched-chain alkyl group containing from 1 to 4 carbon atoms, or represent a halogen, i.e., fluorine, chlorine, bromine or iodine; and R$^4$ is a fluorine, chlorine, bromine or iodine; R$^6$ is a straight or branched chain alkyl or alkoxy group containing from 1 to 4 carbon atoms which may be unsubstituted or substituted by one or more halogen atoms which may be the same or different (the trifluoromethyl and trifluoromethoxy groups are preferred), or a chlorine or bromine atom; and R$^8$ is hydrogen or a fluorine, chlorine, bromine or iodine atom, with the exclusion of the compound wherein R$^1$ represents cyano, R$^2$ represents methanesulphonyl, R$^3$ represents amino, R$^4$ and R$^8$ are chloro and R$^6$ is trifluoromethyl (i.e., the phenyl ring is 2,6-dichloro-4-tri-fluoromethylphenyl), which have valuable activity against arthropod, plant nematode, helminth and protozoan pests, more particularly by ingestion of above preferred compound(s) by the arthropods.

Preferred compounds of the first embodiment of general formula I also include those wherein R$^2$ represents an alkylsuphonyl/sulphinyl/thio group which is optionally halogen substituted containing from 1 to 4 carbon atoms, or an alkenyl- or alkynylsulphonyl/sulphinyl/thio group which is optionally halogen substituted and contains up to 4 carbon atoms, preferably a trifluoromethylthio or trifluoro methylsulphinyl group, R$^3$ represents the hydrogen atom, an amino or methylamino group and R$^1$ represents a halogen atom or preferably the cyano or nitro group.

Compounds of general formula I wherein the phenyl group contains the trifluoromethyl or trifluoromethoxy group, and R$^2$ represents an optionally halogenated alkylsulphonyl/sulphinyl/thio group containing from 1 to 4 carbon atoms are also preferred. Trifluoromethylthio, trifluoromethylsulphinyl and trifluoromethanesulphonyl are especially preferred for R$^2$.

Preferred compounds of the first embodiment of general formula I also include those with phenyl substitution which is 2,4,6-trichloro, 2,6-dichloro-4-difluoromethoxy, 2-chloro-4-trifluoromethyl, 2-bromo-6-chloro-4-trifluoromethyl, 2,6-dibromo-4-trifluoromethyl or 2-bromo-4-trifluoromethyl.

In a most preferred embodiment, the composition comprises the phenyl pyrazole compound known as fipronil, which has the following chemical structure:

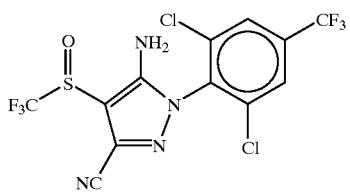

The phenyl pyrazole compound may be present in our composition in an amount ranging from about 0.001 percent by weight to about 5.0 percent by weight. Preferably, the phenyl pyrazole is present at about 0.01 percent by weight to about 1.0 percent by weight. The oil carrier may be present at about 2.0 percent by weight to about 99.99 percent by weight. Preferably, the composition will contain over 50 percent by weight, more preferably over 90 percent by weight.

A "halopyridyl compound," as used herein, refers to the compounds described as halopyridyl compounds in U.S. Pat. No. 3,244,586, the entire contents of which are incorporated herein by reference.

More specifically, the halopyridyl compound used in our composition will have the following chemical structure:

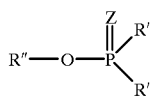

wherein R" represents halopyridyl, Z is selected from the group consisting of oxygen and sulfur, and each R' is individually selected from the group consisting of lower alkoxy, amino, and lower alkylamino.

Preferably, the halopyridyl compound is chlorpyrifos, which has the following chemical structure:

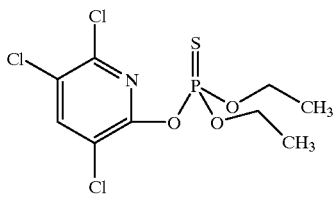

The halo pyridyl compound may be present in our composition in an amount ranging from about 0.01 percent by weight to about 5.0 percent by weight. Preferably, the halo pyridyl is present at about 0.1 percent by weight to about 1.0 percent by weight.

An "avermectin compound" as used herein, refers to compounds described in U.S. Pat. No. 4,310,519, the entire contents of which are incorporated herein by reference.

More specifically, the avermectin compound used in our composition will have the following chemical structure:

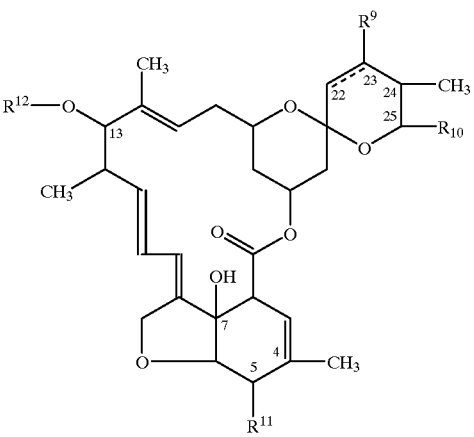

wherein $R^{12}$ is the α-L-oleandrosyl-α-L-oleandroside of the structure:

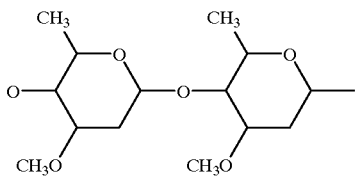

and wherein the broken line indicates a single or a double bond; $R^9$ is hydroxy and is present only when said broken line indicates a single bond, $R^{10}$ is iso-propyl or sec-butyl; and $R^{11}$ is methoxy or hydroxy.

In the foregoing structural formula, the individual compounds are as set forth in the following Table.

| Avermectin | $R^9$ | $R^{10}$ | $R^{11}$ |
| --- | --- | --- | --- |
| A1a | Double bond | sec-butyl | —OCH₃ |
| A1b | Double bond | iso-propyl | —OCH₃ |
| A2a | —OH | sec-butyl | —OCH₃ |
| A2b | —OH | iso-propyl | —OCH₃ |
| B1a | Double bond | sec-butyl | —OH |
| B1b | Double bond | iso-propyl | —OH |
| B2a | —OH | sec-butyl | —OH |
| B2b | —OH | iso-propyl | —OH |

The avermectin compound may be present in our composition in an amount ranging from about 0.001 percent by weight to about 5.0 percent by weight. Preferably, the avermectin is present at about 0.01 percent by weight to about 1.0 percent by weight.

Our composition may additionally contain solvents effective to dissolve the active ingredient. Such solvents include, for example, acetone, dichloromethane, ethyl acetate, methanol, 1-octanol, 2-propanol, N-methyl pyrrolidone, propylene glycol, and ethanol or combinations thereof. About 0 to 5 percent by weight of the solvent may be present in the composition.

The composition may also contain, for example, about 0 to about 10 weight percent of a stabilizer such as sodium stearate. Additionally, the composition may contain any attractants, whether food based or not. Examples of such attractants include Fenugreek™, Furaneol™, aggregation pheromone, sex pheromone, and conventional food based volatile chemicals.

The plant-derived oil carrier used in our composition may include for example, vegetable oil, peanut oil, corn oil, sesame oil, canola oil, linseed oil, rapeseed oil, sunflower oil, palm oil, cottonseed oil, coconut oil, olive oil, safflower oil, soybean oil, or combinations thereof.

Preferably, the oil carrier is in the liquid state at room temperature, i.e. about 21° C. While in the liquid state, the oil carrier facilitates administration of the composition to the area to be treated. The viscosity of the composition may range from about 30 to about 300 cps.

The composition may be applied in any manner to the area where insects, particularly crawling insects such as cockroaches, are to be controlled. Such applications broadly include pressurized spray delivery systems, pump spray delivery systems, and direct application to surfaces within the area with a brush or similar device. Additionally, our composition may be applied to a substrate which is then placed within the area to be treated.

Preferably, the composition is applied in a liquid state, by either direct application to surfaces within the area with a brush or similar device, or by application to at least one substrate which can then be placed within the area. These methods avoid disadvantages associated with a spraying method, and allow application of the composition to a limited area. In a more preferred embodiment, we apply the composition to one or more discrete locations within the area to be treated, as we have surprisingly found that such an application is more effective than application of the composition in a continuous manner over locations having larger surface areas.

As used herein, the term "discrete location" means application of the composition such that less than about 100 droplets are applied within about every 100 square feet of the area to be treated. Preferably about 10 to about 100 droplets are applied within about every 100 square feet to be treated. The term is also intended to embrace embodiments where the composition is first applied to a substrate which is then placed in the area to be treated.

Accordingly, in one preferred embodiment, the composition is applied to one or more discrete locations within the area where the insects are to be controlled by a focused droplet method. In this method, the composition is not sprayed or aerosolized in the area. Instead, droplets are dispensed directly to one or more surfaces within the area by devices such as a brush or similar device, calibrated pipettor, a squeeze bottle, or medicine dropper. As used herein, "droplets" are considered to have a total volume ranging from about 5 to about 75 μl, preferably about 10 to about 50 μl, and even more preferably about 30 to about 50 μl.

In another preferred embodiment, the composition is first applied to a substrate, which is then placed within the area to be treated. In this embodiment, the composition may be applied to the substrate by any known means. Substrates used in this embodiment may be absorbent or nonabsorbent, and include for example paper, tissue paper, or plastics such as high impact polystyrene.

Regardless of the manner in which the composition is to be applied, the composition is preferably used in a non-agricultural setting, i.e. in commercial establishments, industrial settings, or in domestic or household settings.

EXAMPLE 1

0.5 grams of technical fipronil was dissolved in 1 ml of acetone to form a solution. The solution was then blended with 50 g of peanut oil to form a 1 percent by weight composition. 10 microliters of the composition were deposited within a 1 square inch plastic weighing dish to provide a total of 0.1 mg of fipronil.

Comparative Example 2

A commercially available suspension concentrate containing 20 percent by weight of fipronil was deposited in a 1 square inch weighing dish, the suspension concentrate, sold as Regent 1.67 SCTM by Rhone Poulenc, was diluted so that 0.5 mg of fipronil was deposited in the weighing dish.

Comparative Example 3

A commercially available emulsifiable concentrate containing 30 percent by weight of fipronil was also deposited in a 1 square inch weighing dish. The emulsifiable concentrate, sold as Regent 2.3 ECTM by Rhone Poulenc was first diluted so that 0.5 mg of fipronil was added to the weighing dish.

EXAMPLE 4

The contact activities of the fipronil containing compositions of Example 1 and Comparative Examples 2 and 3 were evaluated. For each composition, a test chamber was constructed having an 18×12×8 inch plastic container attached to a second container of the same dimensions with a 2×¾ inch piece of plastic tubing. Both containers were provisioned with harborage food, water, and paper baffles to increase the insect foraging area. The second container additionally contained a fipronil containing composition from one of the above mentioned Examples.

One hundred German cockroaches, *Blattella germanica,* were added to the first container, and access through the tubing was blocked for 3 days to provide an acclimation period. The number of dead cockroaches per 100 was recorded after each of the first four days after access through the tubing was cleared.

TABLE 1

| Treatment | Mean % Mortality at Day 1 | Mean % Mortality at Day 2 | Mean % Mortality at Day 3 | Mean % Mortality at Day 4 |
|---|---|---|---|---|
| Example 1 | | | | |
| 0.1 mg fipronil/peanut oil | 52 | 81 | 94 | 97 |
| Comp. Ex. 2 | | | | |
| 0.5 mg fipronil/ suspension concentrate | 14 | 47 | 64 | 72 |
| Comp. Ex. 3 | | | | |
| 0.5 mg fipronil/ emulsifiable concentrate | 49 | 68 | 82 | 84 |

The data in Table 1 surprisingly reveal that despite a five-fold lower fipronil concentration, the composition containing peanut oil as described in Example 1 performed better than the compositions of Comparative Examples 2 and 3. The results of this example are graphically shown in FIG. 1. The values between the tested compositions are significantly different ($P<0.05$; LT-90).

EXAMPLE 5

The contact activities of 0.1 mg, 0.05 mg, and 0.01 mg the fipronil composition described in Example 1 were compared with 0.1 mg of fipronil dissolved in acetone and tung oil in a manner similar to that described in Example 1. The concentration of the fipronil in tung oil was 0.1 mg/10 $\mu$l of tung oil. Tung oil dries at room temperature after the composition is applied to the area to be treated. The contact activities were evaluated by the method described in Example 4, resulting in the data shown in Table 2.

TABLE 2

| Treatment | Mean % Mortality at Day 1 | Mean % Mortality at Day 2 | Mean % Mortality at Day 3 | Mean % Mortality at Day 4 | Mean % Mortality at Day 7 |
| --- | --- | --- | --- | --- | --- |
| Example 1 | | | | | |
| 0.1 mg fipronil/ peanut oil | 39 | 69 | 84 | 88 | 92 |
| Example 1 | | | | | |
| 0.05 mg fipronil/ peanut oil | 21 | 56 | 70 | 77 | 84 |
| Example 1 | | | | | |
| 0.01 mg fipronil/ peanut oil | 3 | 14 | 37 | 47 | 59 |
| Comp. Ex. 3 | | | | | |
| 0.1 mg fipronil/ emulsifiable concentrate | 1 | 1 | 1 | 1 | 1 |
| 0.1 mg fipronil/ tung oil | 1 | 2 | 3 | 11 | 35 |

The data in Table 2 reveal that fipronil/peanut oil compositions at concentrations as low as 0.01 mg/10 µl perform significantly better than fipronil dissolved in a drying oil such as tung oil, and also significantly better than the emulsifiable concentrate.

EXAMPLE 6

The composition of Example 1 was compared to a composition having 0.5 g of fipronil dissolved in 50 g of soybean oil, and also a composition having 0.5 g of fipronil dissolved in 50 g of partially hydrogenated soybean oil, which was solid at room temperature (i.e. a "soy oil solid"). The contact activities were evaluated by the method described in Example 4, resulting in the data shown in Table 3.

TABLE 3

| Treatment | Mean % Mortality at Day 1 | Mean % Mortality at Day 2 | Mean % Mortality at Day 3 | Mean % Mortality at Day 4 |
| --- | --- | --- | --- | --- |
| Example 1 | | | | |
| 0.1 mg fipronil/peanut oil | 37 | 51 | 58 | 60 |
| 0.1 mg fipronil/ soy oil liquid | 16 | 33 | 41 | 42 |
| 0.1 mg fipronil/ soy oil solid | 3 | 6 | 11 | 13 |

Figure 3:
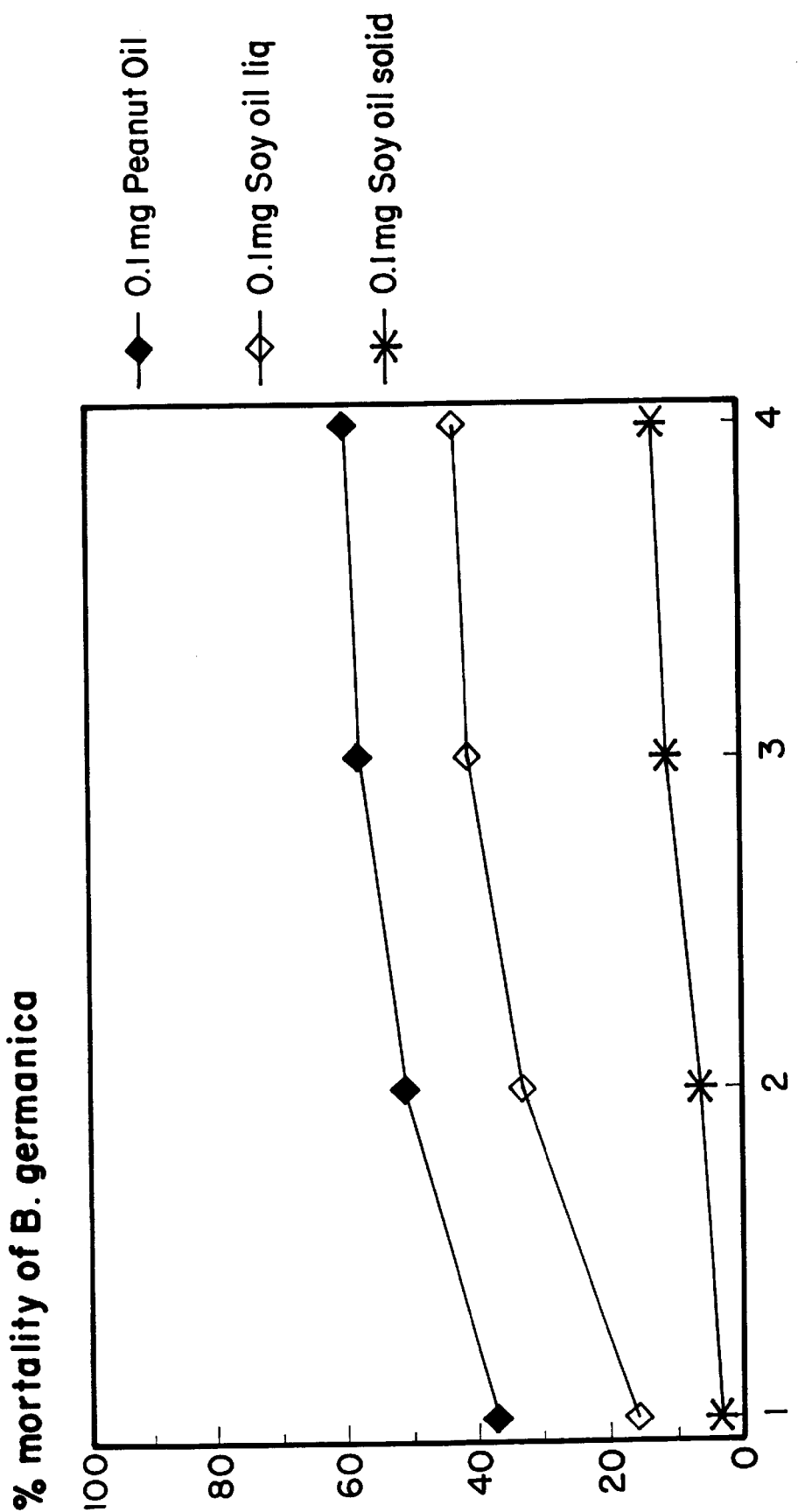
FIG. 3 is a graph comparing the mortality rates of various fipronil compositions with liquid and solid oil carriers.
Figure 4:
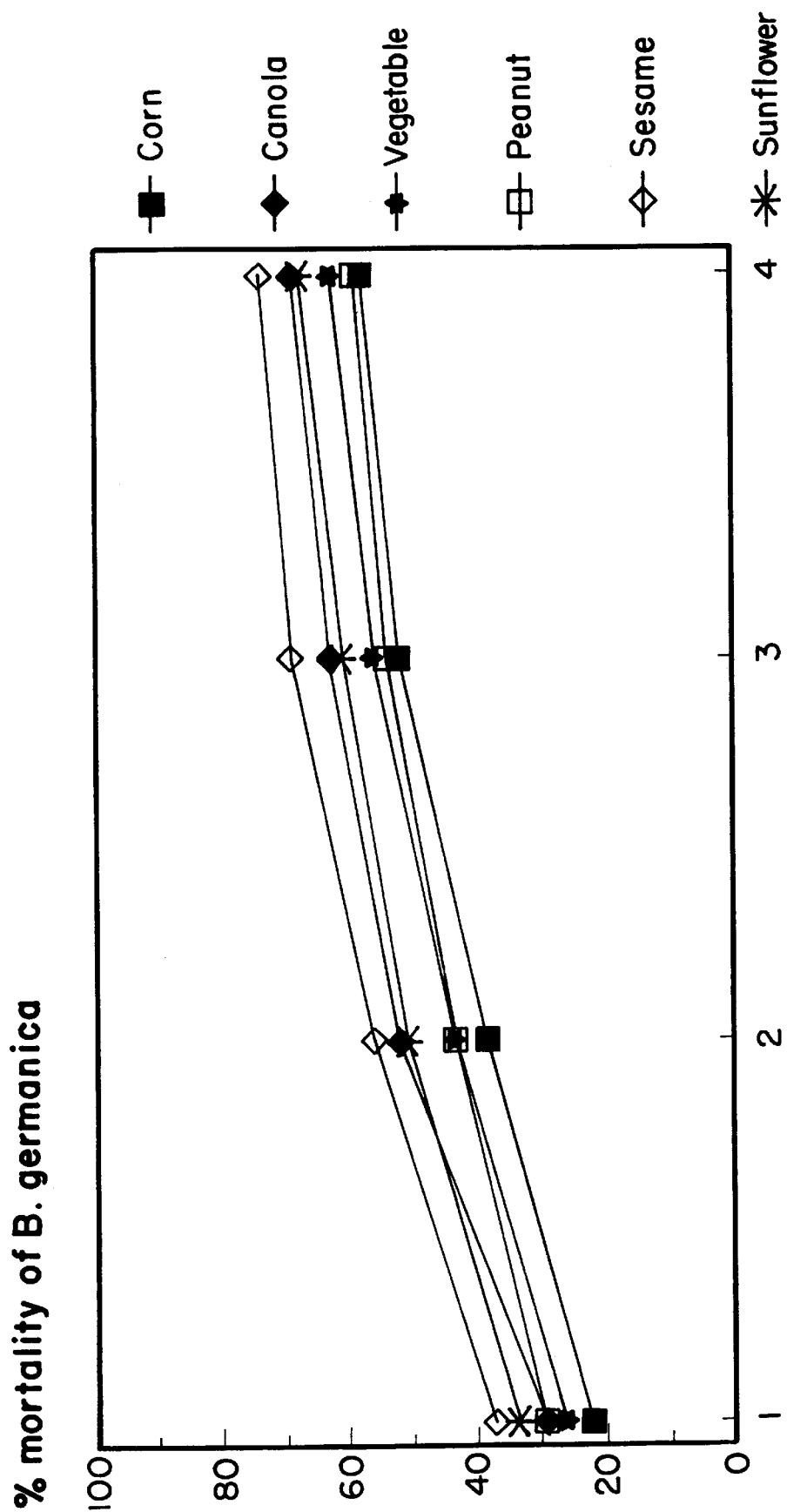
FIG. 4 is a graph comparing the mortality rates of various fipronil compositions with plant-derived oil carriers.

As can be seen in Table 3, and a graph of the data in FIG. 3, both peanut oil and liquid soybean oil are more efficacious oil carriers in combination with fipronil than solid soybean oil, which has been partially hydrogenated.

EXAMPLE 7

Other plant-derived oils which are liquid at room temperature were evaluated in compositions made in a manner analogous to Example 1. Fipronil was dissolved in each oil to give a fipronil concentration of 0.1 mg/10 µl. The contact activities of the compositions were evaluated according to the method described in Example 4, resulting in the data shown in Table 4.

TABLE 4

| Treatment | Mean % Mortality at Day 1 | Mean % Mortality at Day 2 | Mean % Mortality at Day 3 | Mean % Mortality at Day 4 |
| --- | --- | --- | --- | --- |
| Example 1 | | | | |
| 0.1 mg fipronil/peanut oil | 29 | 43 | 54 | 59 |
| 0.1 mg fipronil/corn oil | 22 | 38 | 52 | 58 |
| 0.1 mg fipronil/canola oil | 29 | 52 | 63 | 69 |
| 0.1 mg fipronil/ vegetable oil | 26 | 43 | 56 | 63 |
| 0.1 mg fipronil/sesame oil | 37 | 56 | 69 | 74 |
| 0.1 mg fipronil/ sunflower oil | 33 | 51 | 61 | 68 |

As shown in Table 4, the plant-derived oils tested provide approximately the same level of efficacy as the composition of Example 1.

EXAMPLE 8

The secondary-killing capacity of the fipronil/peanut oil composition of Example 1 was compared with the fipronil suspension concentrate diluted as described in Comparative Example 2. Secondary kill occurs as a result of insecticide being tracked from the original source to other locations by insects visiting the original source. Other insects coming in contact with the tracked insecticide are then killed, thereby enhancing the efficiency of the insecticide.

0.5 mg of each fipronil composition was deposited in a 1 square inch weigh boat. The weigh boat was then placed in a 9 inch diameter container with 10 male German cockroaches. Following death (ca 3 hours), the males and the composition were removed and 30 first-second instar nymphal cockroaches were added. Nymphs were continually added until no more died. Three replicates per treatment were performed.

Figure 5:
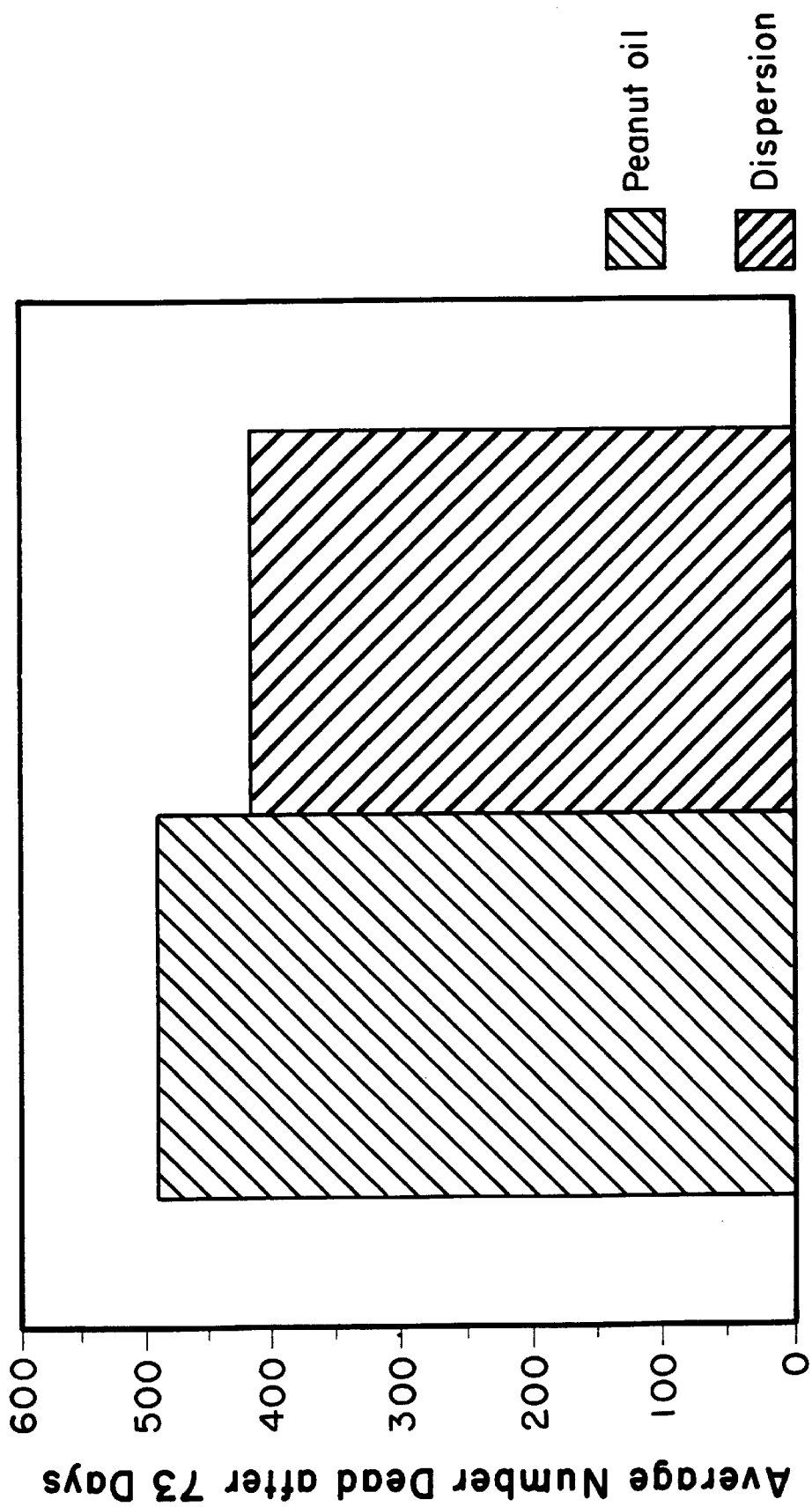
FIG. 5 is a graph comparing the secondary kill rates of various fipronil compositions.
Figure 6:
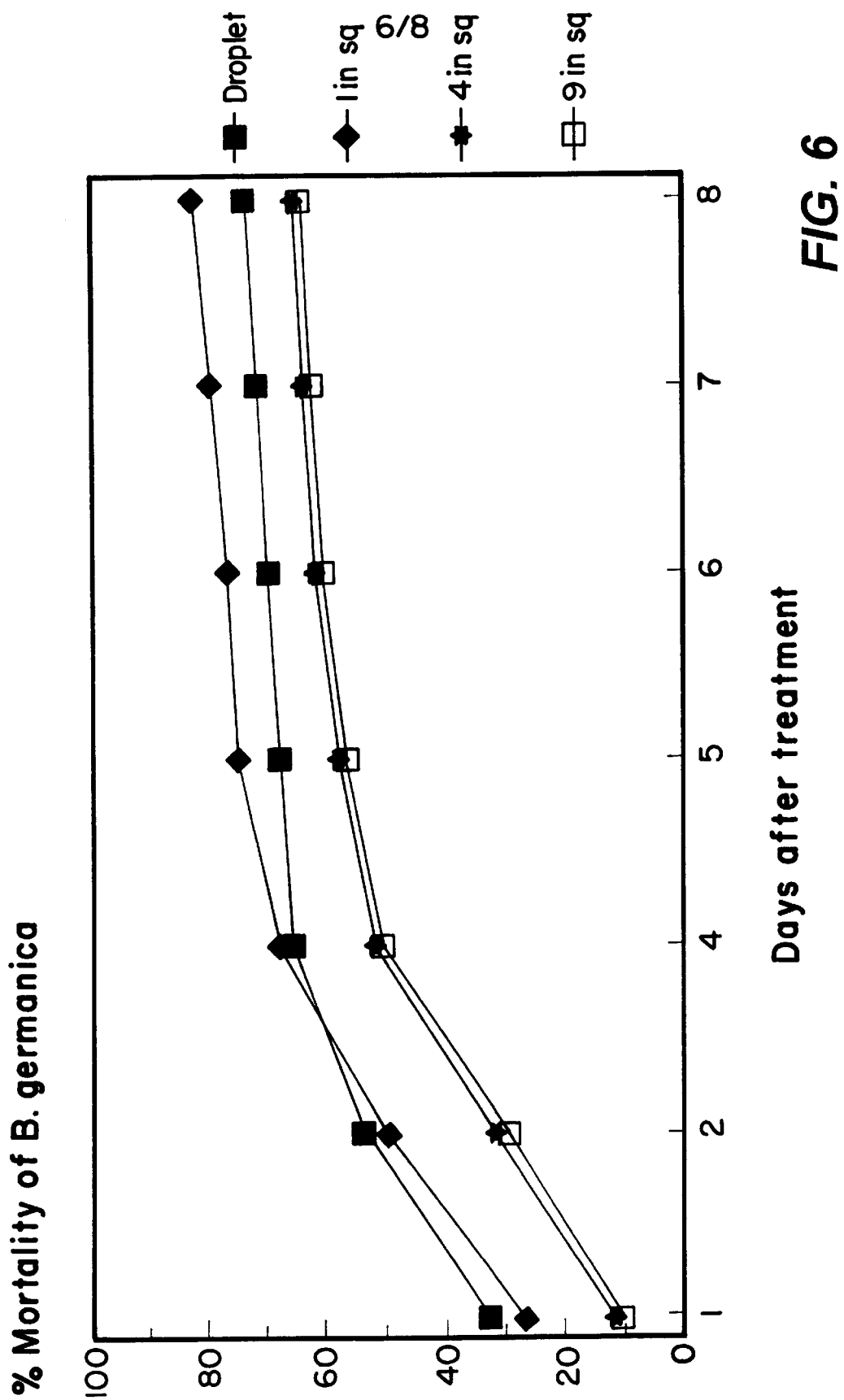
FIG. 6 is a graph comparing the mortality rates of a fipronil composition applied over various surface areas.

Through 73 days, the average number of nymphs killed from the initial 10 males contacting the compositions of Example 1 was 496. The composition of Comparative Example 2 resulted in a lower average secondary kill rate of 418 nymphs. FIG. 5 shows a comparison of these results. These results are statistically different (P<0.05), thus demonstrating the superiority of the composition of Example 1.

EXAMPLE 9

The contact activities of a fipronil composition applied as discrete droplets and the same fipronil composition distributed over a larger area were compared in a laboratory assay. To demonstrate the efficacy of application of the composition as a discrete droplet, 10 µl of the composition of Example 1 were deposited as a droplet in the center of a 9 square inch piece of high impact polystyrene. To demonstrate the efficacy of a continuous and conventional treatment method, 10 µl of the composition of Example 1 were deposited over the entire surface of a 9 square inch piece of high impact polystyrene. Each treated polystyrene piece was placed in a test chamber as described in Example 4, and the contact activities were evaluated as described in Example 4, resulting in the data shown in Table 5.

TABLE 5

| Treatment | Mean % Mortality at Day 1 | Mean % Mortality at Day 2 | Mean % Mortality at Day 4 | Mean % Mortality at Day 5 | Mean % Mortality at Day 6 | Mean % Mortality at Day 7 |
|---|---|---|---|---|---|---|
| Fipronil Droplet | 32 | 53 | 65 | 67 | 69 | 71 |
| Fipronil - 1 inch sq. | 26 | 49 | 67 | 74 | 76 | 79 |
| Fipronil - 4 inch sq. | 11 | 31 | 51 | 57 | 61 | 63 |
| Fipronil - 9 inch square | 10 | 29 | 50 | 56 | 59 | 61 |

As demonstrated by the above data, application of the composition as a discrete droplet outperformed the same composition when spread over the larger area. The time/mortality results between treatments in Table 5 were statistically different ($p<0.05$; Weibull analysis).

EXAMPLE 10

Secondary-kill effects between a fipronil composition applied as discrete droplets and the same fipronil composition distributed over a larger area were compared in a laboratory assay. To demonstrate the efficacy of application of the composition as a discrete droplet, 10 μl of the composition of Example 1 was deposited as a droplet in the center of a 9 square inch piece of high impact polystyrene. To demonstrate the efficacy of a continuous and conventional treatment method, 10 μl of the composition of Example 1 was deposited over the entire surface of a 9 square inch piece of high impact polystyrene.

Each treated polystyrene piece was placed in a 9 inch diameter plastic container. One adult male cockroach was placed in the container. After the cockroach died, it was removed from the container along with the polystyrene. Ten male cockroaches were subsequently placed in containers. The only contact these cockroaches had with the fipronil containing composition was with the composition tracked from the original male to the treated plastic. Dead, secondarily killed cockroaches were counted, recorded, then removed. Cockroaches were continually added until mortality was no longer noted.

Figure 7:
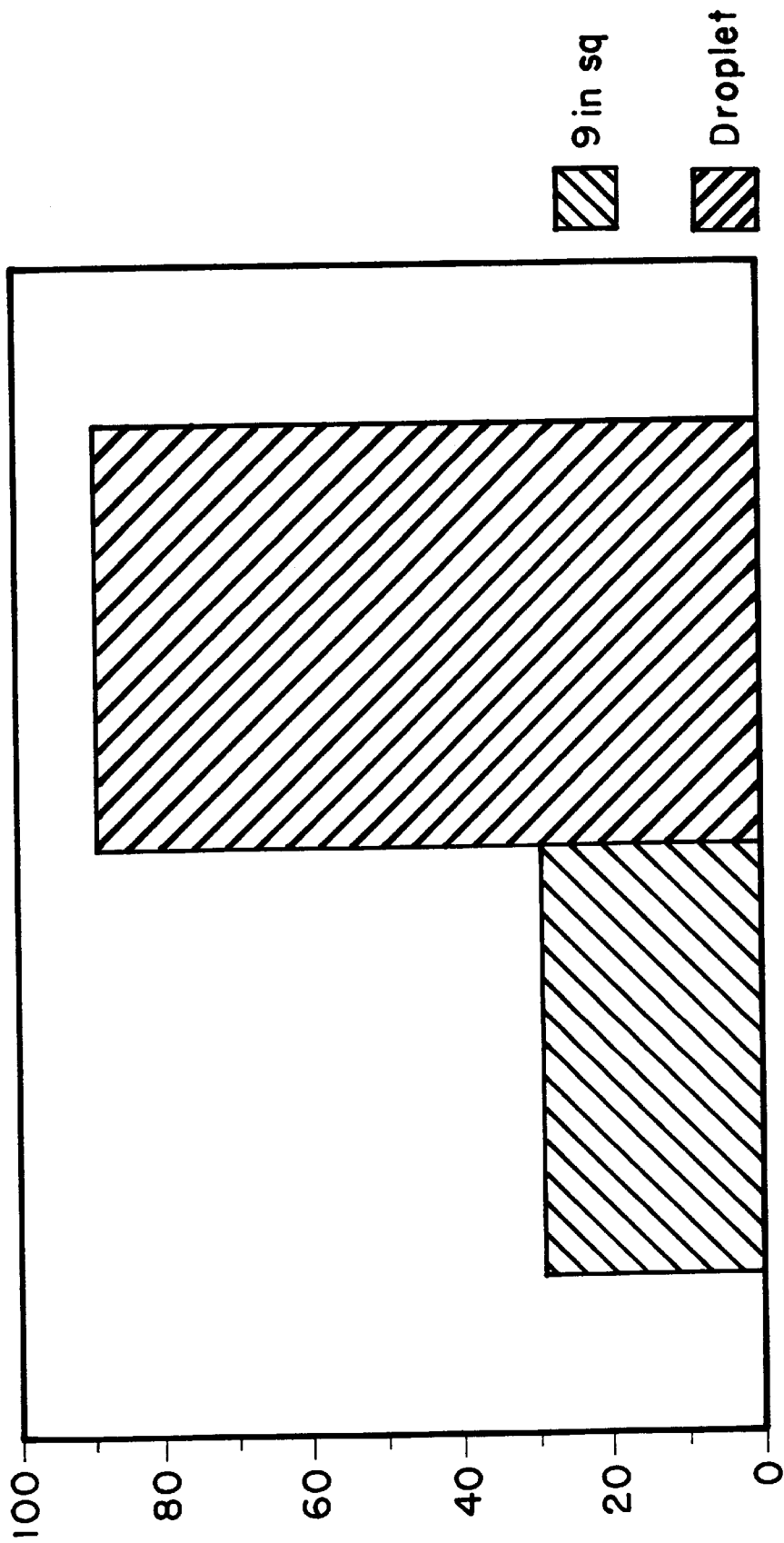
FIG. 7 is a graph comparing the secondary kill rates of a fipronil composition applied over various surface areas.

When fipronil was applied over the entire 9 square inch substrate, after the original male was killed and the treated polystyrene removed, an average of 28.6 additional cockroaches were killed. Fipronil applied as a discrete droplet resulted in a LAW OFFICES secondary kill averaging 89.3 cockroaches. These results are graphically shown in FIG. 7. Thus, the discrete droplet produced a mortality over three times of the continuous distribution of the fipronil composition over the treated area.

EXAMPLE 11

A method of applying our composition in discrete droplets was tested in apartments. Cockroach population levels were assessed prior to treatment by trapping insects overnight in a sticky trap. The day after this assessment was made, infested apartments received treatments of either 2 percent by weight fipronil in peanut oil, 2 percent by weight emulsifiable concentrate, or no treatment. Each treated apartment received one hundred droplets of the composition (ca 40 μl/drop). The performance of each treatment was assessed by trapping cockroaches 2, 7, and 21 days after the treatments were applied, and the following data were collected.

TABLE 6

| Treatment | % Cockroach Reduction at Day 2 | % Cockroach Reduction at Day 7 | % Cockroach Reduction at Day 21 |
|---|---|---|---|
| Fipronil/Peanut Oil | 81a | 89a | 95a |
| Fipronil/Emulsifiable Concentrate | 13b | 84a | 93a |
| Untreated | 0b | 43b | 61b |

Figure 8:
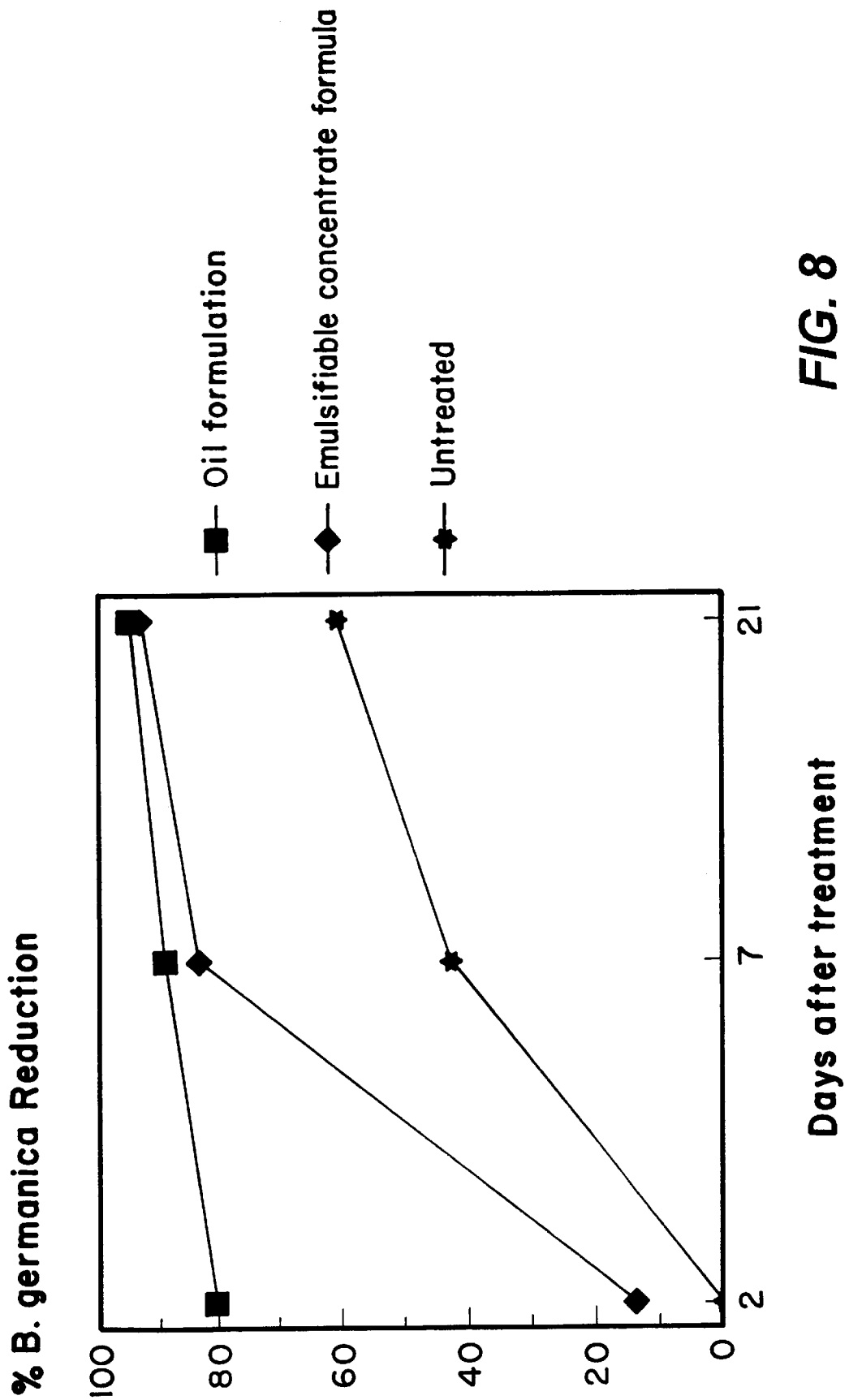
FIG. 8 is a graph comparing the mortality rates of various fipronil compositions applied in cockroach infested apartments.

Mortality figures in Table 6 followed by the same letter within a column are not significantly different from one another. The data in Table 6, and also shown in FIG. 8, reveal that the method of applying our composition as discrete droplets had dramatically superior effect on the cockroach population after the second day of treatment.

It will be apparent to those skilled in the art that various modifications and variations can be made in the composition and method disclosed above without departing from the spirit of our discovery. Thus, it is intended that our description covers the modifications and variations of this invention provided that they come within the scope of the appended claims and their equivalents.

We claim:

1. A composition consisting essentially of an active ingredient in an amount toxic to insects wherein the active ingredient is selected from the group consisting of a phenyl pyrazole compound, a halopyridyl compound, and an avermectin compound; or combinations thereof, and a plant-derived oil carrier.

2. The composition of claim 1, wherein the active ingredient is a phenyl pyrazole compound having the following structure:

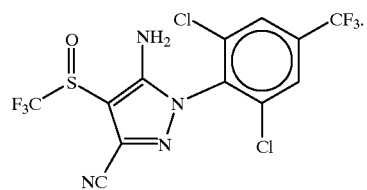

3. The composition of claim 1, wherein the active ingredient is a halopyridyl compound having the following structure:

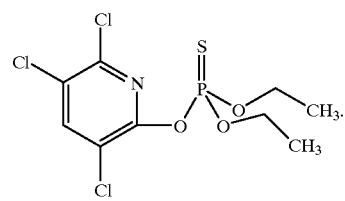

4. The composition of claim 1, wherein the active ingredient is an avermectin compound having the following structure:

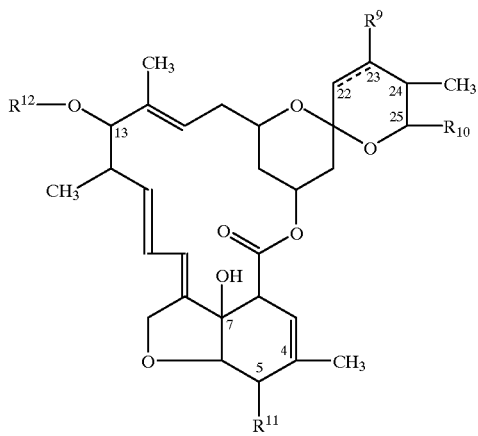

wherein $R^{12}$ is the α-L-oleandrosyl-α-L-oleandroside of the structure

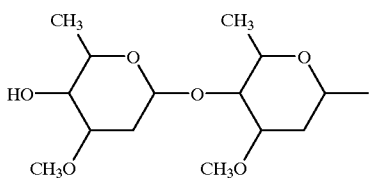

wherein the broken line indicates a single or a double bond; $R^9$ is hydroxy and is present only when said broken line indicates a single bond, $R^{10}$ is iso-propyl or sec-butyl; and $R^{11}$ is methoxy or hydrogen.

5. The composition of claim 1, wherein the plant-derived oil carrier is peanut oil, corn oil, vegetable oil, canola oil, coconut oil, cottonseed oil, linseed oil, rapeseed oil, olive oil, palm oil, sesame oil, safflower oil, sunflower oil, or soybean oil, or combinations thereof.

6. The composition of claim 1, wherein the plant-derived oil carrier is a liquid at room temperature.

7. The composition of claim 1, wherein the phenyl pyrazole compound is present in an amount of about 0.01 percent by weight to about 5.0 percent by weight.

8. The composition of claim 1, wherein the plant-derived carrier is present in an amount of about 2.0 percent by weight to about 99.99 percent by weight.

9. A composition consisting essentially of an active ingredient in an amount toxic to insects wherein the active ingredient is selected from the group consisting of a phenyl pyrazole compound, a halopyridyl compound, and an avermectin compound; or combinations thereof, a plant-derived oil carrier, and a stabilizer.

10. The composition of claim 1, wherein the composition is located on a substrate.

11. The composition of claim 10, wherein the substrate is an absorbent material.

12. The composition of claim 10, wherein the substrate is paper, tissue paper, cardboard, or plastic.

13. The composition of claim 10, wherein the substrate's surface area contacting the composition is less than about 100 square inches.

14. The composition of claim 10, wherein the substrate's surface area contacting the composition is less than or equal to about 10 square inches.

15. The composition of claim 10, wherein the total surface area of the substrate is less than or equal to about 100 square inches.

16. A method of controlling insects, which method consisting essentially of application of a composition consisting essentially of
 (a) an active ingredient selected from the group consisting of a phenyl pyrazole compound, a halopyridyl compound, and an avermectin, and
 (b) a plant-derived oil carrier;
to an area where the insects are to be controlled.

17. The method of claim 16, wherein the active ingredient is a phenyl pyrazole compound having the following structure:

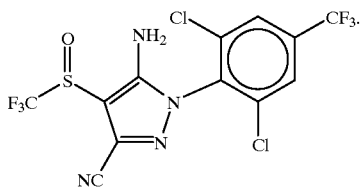

18. The method of claim 16, wherein the active ingredient is a halopyridyl compound having the following structure:

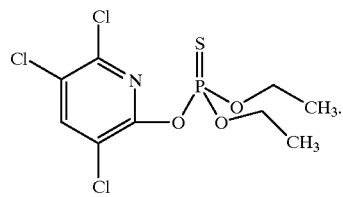

19. The method of claim 16, wherein the active ingredient is an avermectin compound having the following structure:

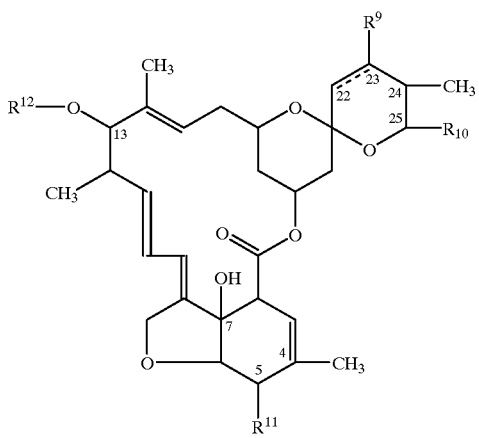

wherein $R^{12}$ is the α-L-oleandrosyl-α-oleandroside of the structure

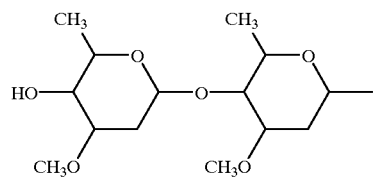

and wherein the broken line indicates a single or a double bond; $R^9$ is hydroxy and is present only when said broken line indicates a single bond, $R^{10}$ is iso-propyl or sec-butyl; and $R^{11}$ is methoxy or hydroxy.

20. The method of claim 16, wherein the composition is applied within the area in more than one discrete location.

21. The method of claim 16, wherein the composition is applied to at least one surface within the area.

22. The method of claim 16, wherein about 10 to about 100 droplets of the composition are applied within every 100 square feet of the area.

23. The method of claim 16, wherein the composition is applied to the area by spraying, brushing, blotting, or dropping.

24. The method of claim 16, wherein the composition is first applied to a substrate, and then the substrate is placed within the area.

25. The method of claim 24, wherein the substrate is an absorbent material.

26. The method of claim 24, wherein the substrate is paper, tissue paper, cardboard, or plastic.

27. The method of claim 16, wherein the composition is directly applied to at least one surface within the area.

28. The method of claim 16, wherein the insects are cockroaches.

29. The method of claim 16, wherein the plant-derived oil carrier is liquid at room temperature.

30. The method of claim 16, wherein the plant-derived oil carrier is peanut oil, corn oil, vegetable oil, canola oil, coconut oil, linseed oil, rapeseed oil, cottonseed oil, olive oil, palm oil, sesame oil, sunflower oil, safflower oil, soybean oil, or combinations thereof.

31. The method of claim 16, wherein the phenyl pyrazole compound is present in an amount of about 0.01 percent by weight to about 5.0 percent by weight.

32. The method of claim 16, wherein the plant-derived carrier is present in an amount of about 2.0 percent by weight to about 99.99 percent by weight.

* * * * *